United States Patent
Peltola et al.

(10) Patent No.: US 10,625,096 B2
(45) Date of Patent: Apr. 21, 2020

(54) RADIATION THERAPY TREATMENT PLANNING AND USAGE

(71) Applicant: Varian Medical Systems International AG, Cham (CH)

(72) Inventors: Jarkko Y. Peltola, Tuusula (FI); Janne I. Nord, Espoo (FI)

(73) Assignee: Varian Medical Systems International AG, Steinhausen (CH)

( * ) Notice: Subject to any disclaimer, the term of this patent is extended or adjusted under 35 U.S.C. 154(b) by 909 days.

(21) Appl. No.: 14/865,765

(22) Filed: Sep. 25, 2015

(65) Prior Publication Data
US 2017/0087383 A1    Mar. 30, 2017

(51) Int. Cl.
*A61N 5/10* (2006.01)

(52) U.S. Cl.
CPC .... *A61N 5/1031* (2013.01); *A61N 2005/1041* (2013.01); *A61N 2005/1074* (2013.01)

(58) Field of Classification Search
CPC .. A61N 5/1031; A61N 5/1036; A61N 5/1037; A61N 5/1038; A61N 5/1039; A61N 2005/1032; A61N 2005/1034; A61N 2005/1035
See application file for complete search history.

(56) References Cited

U.S. PATENT DOCUMENTS

| | | | |
|---|---|---|---|
| 7,831,289 B2 | 11/2010 | Riker et al. | |
| 2005/0111621 A1* | 5/2005 | Riker | A61N 5/1031 378/65 |
| 2006/0293583 A1* | 12/2006 | Saracen | A61N 5/1038 600/407 |
| 2011/0065974 A1* | 3/2011 | Rietzel | A61N 5/103 600/1 |
| 2013/0197878 A1* | 8/2013 | Fiege | A61N 5/1031 703/2 |

* cited by examiner

*Primary Examiner* — Carrie R Dorna
(74) *Attorney, Agent, or Firm* — Fitch, Even, Tabin & Flannery LLP (57) ABSTRACT

A control circuit forms a radiation therapy treatment plan. By one approach this comprises displaying a structure dose volume histogram on a display and detecting when a user directly manipulates the displayed structure dose volume histogram. In response to detecting that manipulation the control circuit uses a corresponding virtual set of optimization objectives to optimize a radiation therapy treatment plan. If desired, the control circuit can also use weighted optimization objectives when optimizing the radiation therapy treatment plan. Also if desired, the control circuit can use only a low-resolution approximate geometry to represent a particular trajectory as corresponds to different exposure fields for the radiation therapy to be administered when initially optimizing the radiation therapy treatment plan. The control circuit can then subsequently use a high-resolution geometry to represent that trajectory to further optimize the radiation therapy treatment plan.

17 Claims, 6 Drawing Sheets

RADIATION THERAPY TREATMENT PLANNING AND USAGE

TECHNICAL FIELD

These teachings relate generally to the use of radiation as a therapeutic treatment and more specifically to the formation and use of corresponding radiation-treatment plans.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted areas and adjacent healthy tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient. Such treatment plans are often optimized prior to use. (As used herein, "optimization" will be understood to refer to improving upon a candidate treatment plan without necessarily ensuring that the optimized result is, in fact, the singular best solution.) Many optimization approaches use an automated incremental methodology where various optimization results are calculated and tested in turn using a variety of automatically-modified (i.e., "incremented") treatment plan optimization parameters.

Treatment plans are typically generated as a function of user-specified dosimetric goals. Generally speaking, a well-conceived radiation-treatment plan serves to help ensure that the treatment target receives a prescribed dose of radiation while avoiding, to as large an extent as might be possible, undue dosing of surrounding or intervening tissues and organs.

BRIEF DESCRIPTION OF THE DRAWINGS

Various needs are at least partially met through provision of the radiation therapy treatment planning and usage described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments a control circuit forms a radiation therapy treatment plan. By one approach this comprises displaying a structure dose volume histogram on a display and detecting when a user directly manipulates the displayed structure dose volume histogram. In response to detecting that manipulation the control circuit uses a corresponding virtual set of optimization objectives to optimize a radiation therapy treatment plan. If desired, the control circuit can also use weighted optimization objectives when optimizing the radiation therapy treatment plan. Also if desired, the control circuit can use only a low-resolution approximate geometry to represent a particular trajectory as corresponds to different exposure fields for the radiation therapy to be administered when initially optimizing the radiation therapy treatment plan. The control circuit can then subsequently use a high-resolution geometry to represent that trajectory to further optimize the radiation therapy treatment plan.

So configured, user interaction and/or speed/quality of the optimization process can often be improved.

Figure 1:
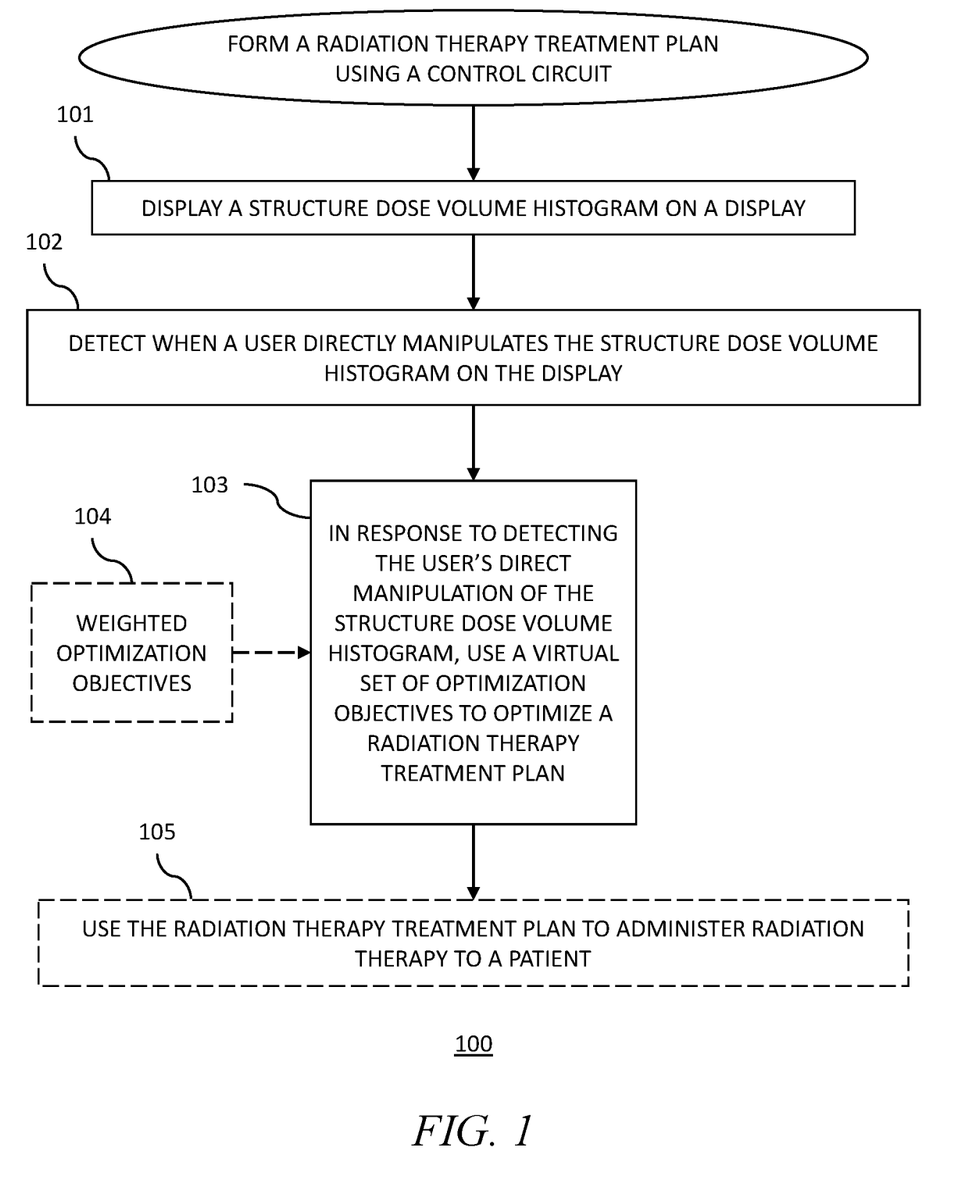
FIG. 1 comprises a flow diagram as configured in accordance with various embodiments of these teachings.
Figure 2:
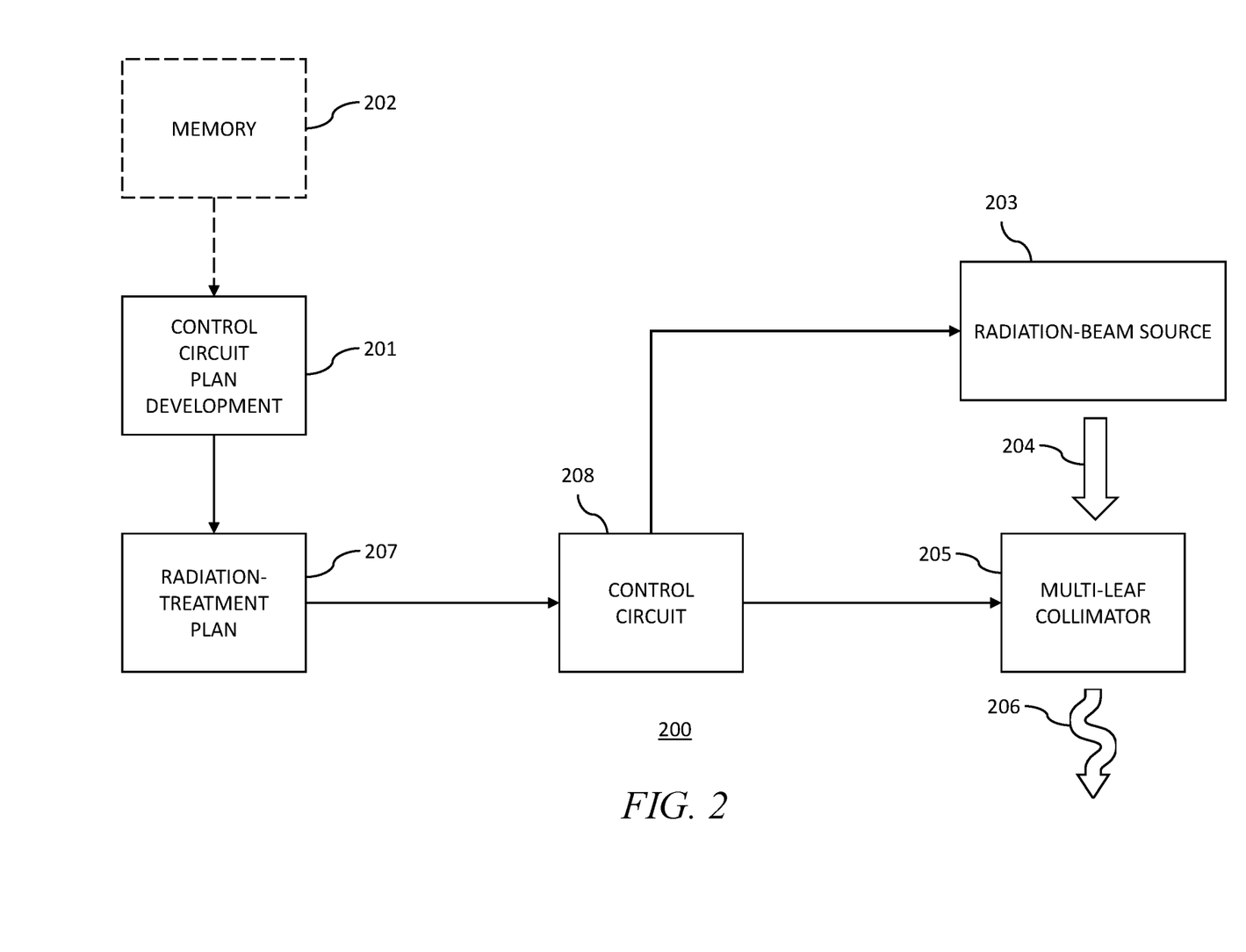
FIG. 2 comprises a block diagram as configured in accordance with various embodiments of these teachings.

These and other benefits may become clearer upon making a thorough review and study of the following detailed description. Referring now to the drawings, and in particular to FIG. 1, an illustrative process 100 that is compatible with many of these teachings will now be presented. For the sake of an illustrative example it will be presumed in this description that a control circuit (or plurality of control circuits) carries out the actions, steps, and functions described in this process 100. FIG. 2 provides an illustrative example in these regards.

As shown in FIG. 2, a radiation therapy treatment platform 200 can include or otherwise operably couple to a control circuit 201. Being a "circuit," the control circuit 201 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 201 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 201 is configured (for example, by using corresponding programming as will be well understood by those skilled in the art) to carry out one or more of the steps, actions, and/or functions described herein. It will also be understood that a "control circuit" can comprise multiple such components or platforms as well as suggested by the phantom control circuit box in FIG. 2.

By one optional approach the control circuit 201 operably couples to a memory 202. This memory 202 may be integral to the control circuit 201 or can be physically discrete (in whole or in part) from the control circuit 201 as desired. This memory 202 can also be local with respect to the control circuit 201 (where, for example, both share a common circuit board, chassis, power supply, and/or housing) or can be partially or wholly remote with respect to the control circuit 201 (where, for example, the memory 202 is physically located in another facility, metropolitan area, or even country as compared to the control circuit 201).

In addition to radiation treatment plans this memory 202 can serve, for example, to non-transitorily store the computer instructions that, when executed by the control circuit 201, cause the control circuit 201 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

The radiation therapy treatment platform 200 also includes a therapeutic radiation beam source 203 that operably couples and responds to a control circuit 208. (In this illustrative example a first control circuit 201 attends to developing the radiation treatment plan 207 while a second control circuit 208 uses that radiation treatment plan 207 to administer radiation therapy to a patient. These teachings will accommodate a segregated architecture as illustrated, but will also readily accommodate using the same control circuit 201 in all of these regards.) So configured, a corresponding radiation beam 204 as emitted by the radiation beam source 203 can be selectively switched on and off by the control circuit 208. These teachings will also accommodate having the control circuit 208 control the relative strength of the radiation beam 204. Radiation sources are well understood in the art and require no further description here.

In this example the radiation beam 204 is directed towards a multi-leaf collimation system 205 that also operably couples to the control circuit 208 to thereby permit the control circuit 208 to control movement of the collimation systems leaves and hence the formation and distribution of one or more radiation-modulating apertures. Multi-leaf collimators are comprised of a plurality of individual parts (known as "leaves") that are formed of a high atomic numbered material (such as tungsten) that can move independently in and out of the path of the radiation-therapy beam in order to selectively block (and hence shape) the beam. Typically the leaves of a multi-leaf collimator are organized in pairs that are aligned collinearly with respect to one another and that can selectively move towards and away from one another via controlled motors.

By passing a therapeutic radiation beam 204 through the aperture(s) of a multi-leaf collimator the radiation beam can be modulated to provide a modulated radiation beam 206 that better matches the dosing requirements of the treatment session. These dosing requirements typically include (or at least presume) prescribing which body tissues to irradiate and which body tissues to avoid irradiating. The resultant modulated radiation beam 206 then reaches a treatment target in a corresponding patient.

With continued reference to FIGS. 1 and 2, at block 101 this process 100 provides for displaying a structure dose volume histogram on a display. Dose volume histograms typically represent three-dimensional dose distributions in a graphical two-dimensional format (the three-dimensional dose distributions being created, for example, in a computerized radiation-treatment planning system based on a three-dimensional reconstruction of an X-ray computed tomography scan and study). The "volume" referred to in dose volume histogram analysis can be, for example, the radiation-treatment target, a healthy organ located near such a target, an arbitrary structure, and so forth.

Figure 3:
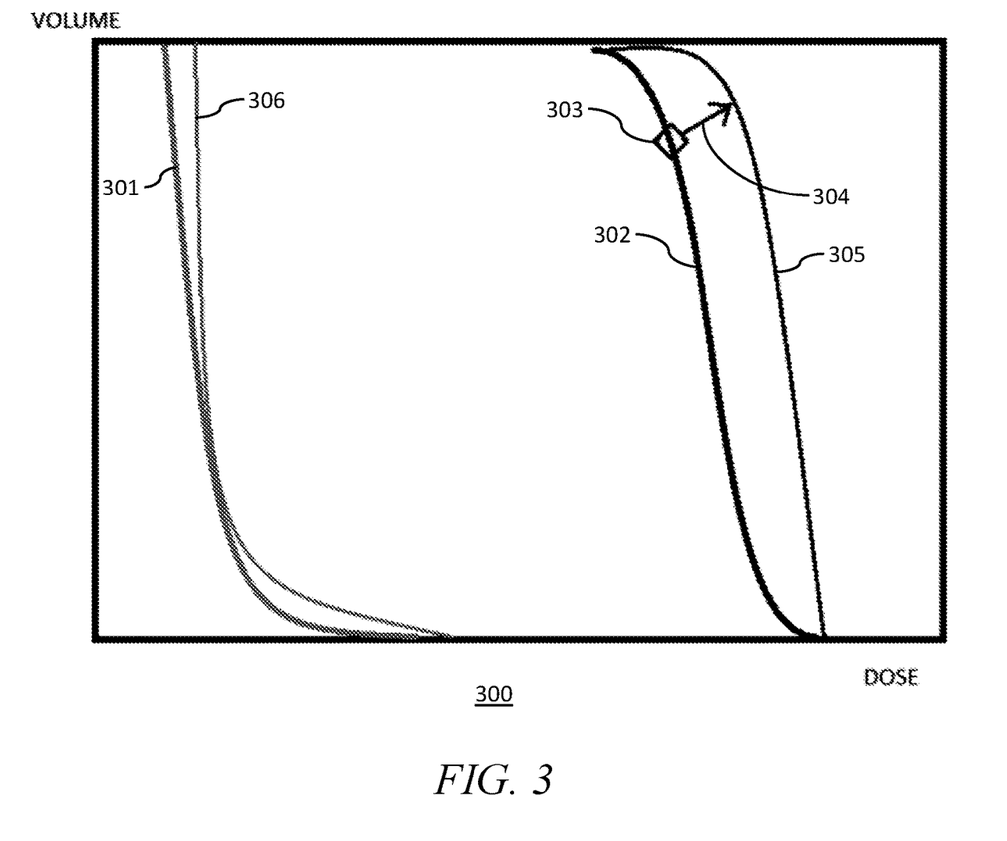
FIG. 3 comprises a display screen shot as configured in accordance with various embodiments of these teachings.

This display activity will typically occur relatively early in the development of a radiation treatment plan. FIG. 3 presents an illustrative example in these regards. In this illustrative example the dose volume histogram display 300 presents two structure dose volume histograms for two different structures. A first dose volume histogram line 301 represents a nontargeted structure and a second dose volume histogram line 302 represents the treatment target for a particular patient. These dose volume histogram lines can be created from knowledge-based objectives that are not necessarily also presented to the user.

These dose volume histogram lines can be textually labeled and/or marked with an icon or other graphical embellishment as desired. These dose volume histogram lines can also be rendered in different colors if desired. For example, the first dose volume histogram line 301 can be rendered in a shade of green while the second dose volume histogram line 302 can be rendered in a different color such as a shade of red.

At block 102 this process 100 provides for detecting when a user directly manipulates the structure dose volume histogram on the display. As used herein, this reference to "directly manipulating" the structure dose volume histogram refers to directly manipulating the rendered line itself. In this illustrative example the display comprises a touch-sensitive display and the user has touched the screen where indicated by reference numeral 303 and then moved their fingertip across the display as represented by the arrow denoted by reference numeral 304. This process 100 will accommodate other approaches to such direct manipulation. For example, these teachings will accommodate indicating a point on the dose volume histogram line with a cursor and then clicking and dragging that point elsewhere on the display.

This reference to "direct manipulation," however, does not include, for example, manipulating some displayed marker on the screen that is positioned aside from one of the dose volume histogram lines nor, for example, changing numeric values in a displayed field, spreadsheet matrix, or the like.

At block 103, the control circuit responds to detecting the user's direct manipulation of the structure dose volume histogram by using a virtual set of optimization objectives to optimize a radiation therapy treatment plan. By one approach the control circuit creates that virtual set of optimization objectives at this time in order to permit such usage. This activity can comprise creating a new virtual objective to match the user's change. Generally speaking, for many application settings there is no need to display or otherwise present these virtual objectives to the user.

For many application settings it will be beneficial to create a set of virtual objectives for each dose volume histogram inside the optimizer.

As one example in these regards, the control circuit can use the location to where the user manipulated a part of the structure dose volume histogram line to define a new dose volume histogram objective. The foregoing usage can comprise, in turn, using the virtual set of optimization objectives to favor holding at least one of the structure dose volume histograms in a same position. As optimization proceeds the optimizer can be configured to try to keep changes in every other dose volume histogram as minimal as possible.

In those regards, and referring again to FIG. 3, by one approach the new dose volume histogram lines 305 and 306 for both of the two structures (in this example) can be simultaneously displayed with the old, original dose volume histogram lines 302 and 301 to provide the user with a clear visual sense of how the user's manipulation of the structure dose volume histogram line 302 more universally affected the results. More particularly, though the virtual objectives are not directly presented, the corresponding cost generated by those virtual objectives is well illustrated in a visual manner easily understood by the viewer.

By one approach, when the user accepts that change the originally-displayed structure dose volume histogram lines 301 and 302 can be removed from the display leaving only the new, modified structure dose volume histogram lines 305 and 306.

By one approach, if desired, the control circuit can also use weighted optimization objectives 104 when optimizing the radiation therapy treatment plan. As one example in these regards, historical information can be used to produce those weighted optimization objectives (where, for example, that historical information provides an estimation regarding structure dose volume histograms that are achievable for the patient).

Figure 4:
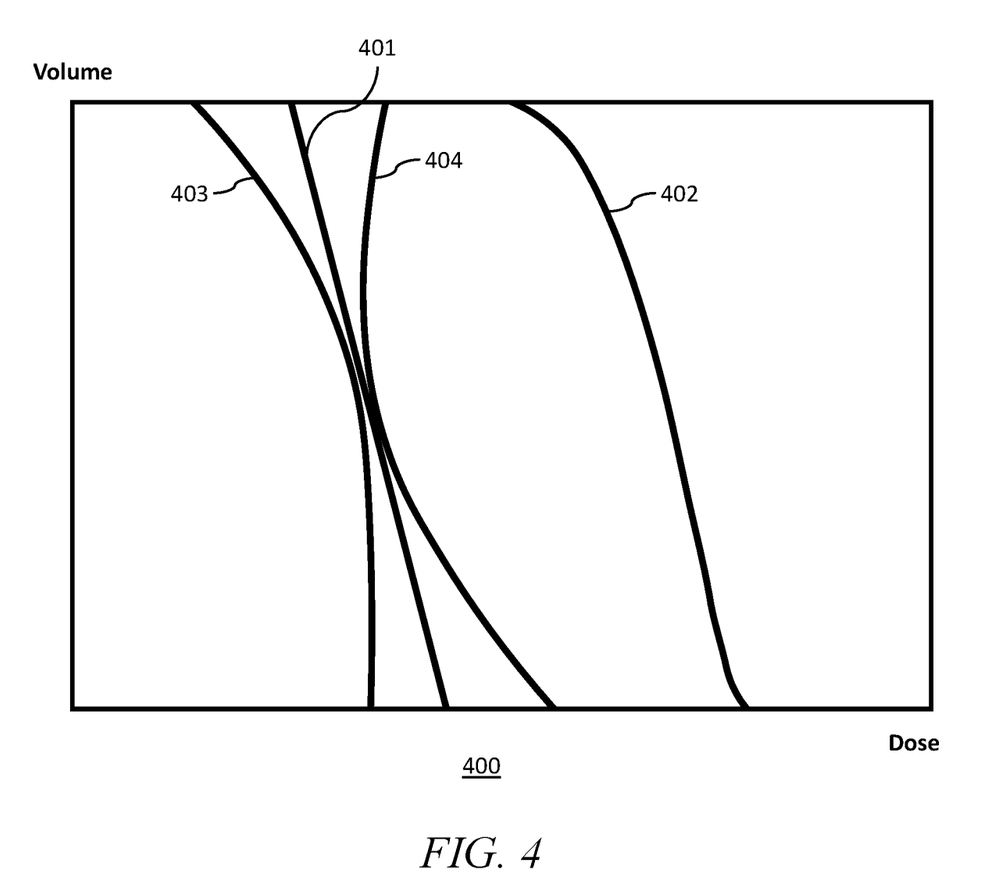
FIG. 4 comprises a graph as configured in accordance with various embodiments of these teachings.

The control circuit can use such weighted optimization objectives to optimize the radiation therapy treatment plan by allowing those weighted optimization objectives to influence which parts of a structure dose volume histogram are permitted to change to a greater extent than other parts of the structure dose volume histogram during user interaction. FIG. 4 presents a relevant example in these regards. In this example the display 400 presents two structure dose volume histogram lines 401 and 402. Weighted optimization objectives 403 and 404 are distributed along the first line with the shape of those weighted optimization objectives varying along that line depending upon a distance between variance curves that represent the historical information.

Presenting such information can offer the user with a largely intuitive visual cue regarding what further changes may or may not be possible or advisable.

With continued reference to FIGS. 1 and 2, in some cases administering the radiation therapy to the patient will entail moving the radiation source 203 with respect to the patient along a particular trajectory (such as an arc-shaped trajectory) to a plurality of different exposure fields. In such a case, and if desired, these teachings will also encompass optimizing a radiation therapy treatment plan that includes the steps shown in FIG. 5.

Figure 5:
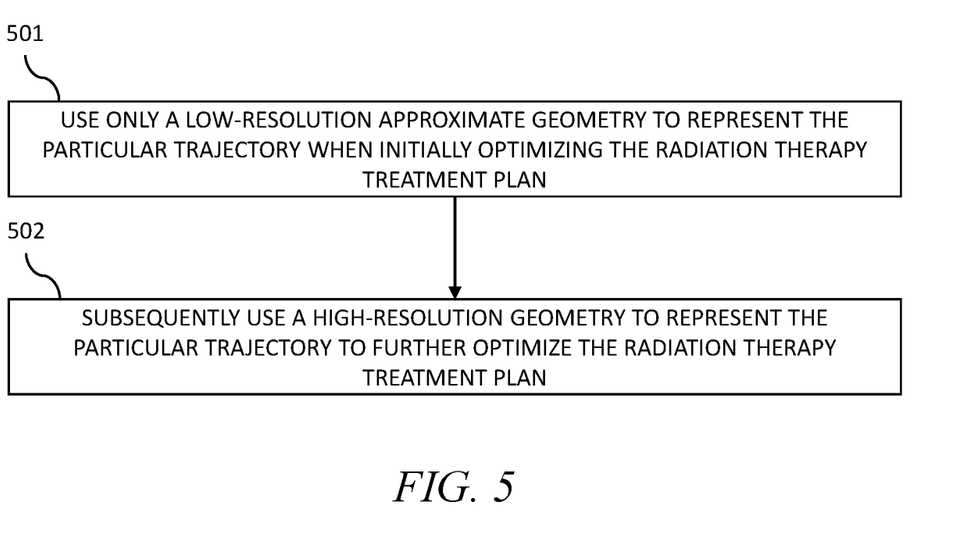
FIG. 5 comprises a flow diagram as configured in accordance with various embodiments of these teachings.
Figure 6:
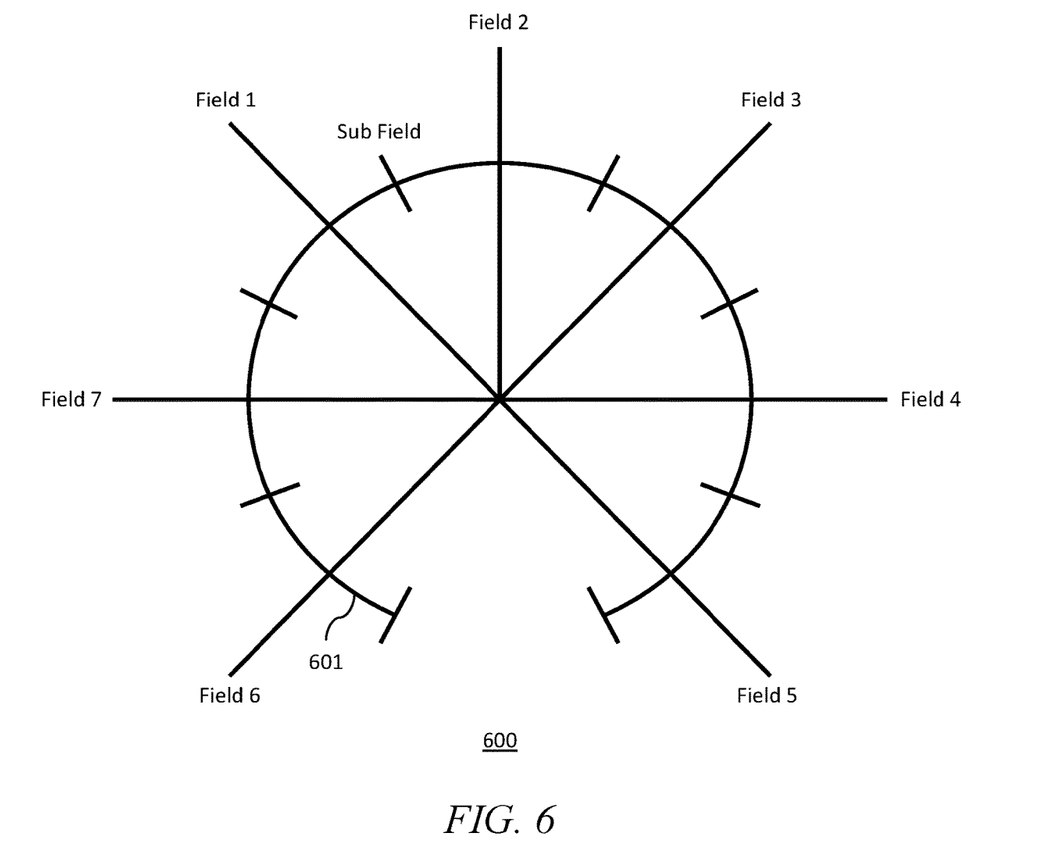
FIG. 6 comprises a schematic trajectory view as configured in accordance with various embodiments of these teachings.

In particular, at block 501 the control circuit uses only a low-resolution approximate geometry to represent the trajectory when initially optimizing the radiation therapy treatment plan. By one approach this step contemplates forming or representing the low-resolution approximate geometry by dividing the particular trajectory into only a low number of subparts. As an illustrative example, FIG. 6 depicts a trajectory 601 that comprises nearly a complete circle. In such a case, the low-resolution approximate geometry may represent dividing that trajectory 601 into only seven fields (most of which are spaced generally equidistant from one another in this illustrative example). Generally speaking, it can be useful in many application settings for the particular locations used in these regards to comprise key angles; i.e., radiation-exposure angles that are relatively different from one another and/or that may correspond to a particular exposure angle where it may be particularly important to control, for example, avoiding undue exposure to a non-targeted volume in the patient.

By one approach this use of only low-resolution approximate geometry to represent the particular trajectory when initially optimizing the radiation therapy treatment plan can yield as an output a set of fluence maps corresponding to particular locations of the particular trajectory. (Fluence represents radiative flux integrated over time and comprises a fundamental metric in dosimetry (i.e., the measurement and calculation of an absorbed dose of ionizing radiation in matter and tissue).)

At block 502 the control circuit can then subsequently use a high-resolution geometry to represent the particular trajectory to further optimize the radiation therapy treatment plan. This reference to high-resolution geometry shall be understood to refer in a relative way to the low-resolution geometry described above. Accordingly, however course or fine the resolution may be for the so-called low-resolution approximate geometry, the high-resolution geometry shall constitute a higher-resolution geometry than that employed for the low-resolution geometry.

The foregoing bifurcated approach can be viewed as employing two distinct phases; i.e., a drafting phase and an optimizing phase. The fluence maps from the drafting phase need not be used as input information when optimizing for an arc-shaped trajectory. Instead, a drafted dose matrix (and the corresponding dose volume histograms that can be directly calculated from the dose, presuming knowledge regarding the corresponding structures) can be used as the input information for the latter. These two phases can be separated by time when using the same computational platform or by machine type as desired.

The output of this particular process can comprise dose distribution information and dose volume histograms per structure. This output can then be directly utilized when optimizing the radiation treatment plan.

So configured, machine control information (for example, fluencies, machine control points, multi-leaf collimator leaf parameter settings, and so forth) produced by the low-resolution-based optimization is not used by the high-resolution-based optimization. The first optimization geometry will preferably approximate the second optimization geometry but the two do not have to exactly match. For example, different collimator angles can be used during the high-resolution-based optimization if desired.

It will be appreciated that the foregoing teachings are highly flexible in practice. Referring to the low-resolution/high-resolution approach just described, for example, if desired the first optimization can be accomplished and the output then saved. The second optimization can then be performed later as often as desired for any number of slightly different patient images (to accommodate, for example, a patient gaining or losing weight over the course of an extended series of treatments).

At block 105 this process 100 then provides for using the aforementioned radiation therapy treatment plan to administer radiation therapy to a patient. Using a treatment platform in these regards comprises a well-understood area of prior art endeavor and accordingly further elaboration is not provided here for the sake of brevity.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method comprising:
   forming a radiation therapy treatment plan using a control circuit by:
   displaying at least two structure dose volume histograms for two different structures on a display;
   detecting when a user directly manipulates at least one of the at least two structure dose volume histograms on the display;
   in response to detecting the user's manipulation of at least one of the at least two structure dose volume histograms, presenting on the display both new and old dose volume histograms for both of the two different structures until the user accepts the manipulation;
   in response to detecting that the user accepts the manipulation, removing from the display the old dose volume histograms while leaving the new dose volume histograms on the display;
   also in response to detecting that the user accepts the manipulation, using a virtual set of optimization objectives to optimize a radiation therapy treatment plan;
   using the radiation therapy treatment plan to administer radiation therapy to a patient.

2. The method of claim 1 wherein displaying the at least two structure dose volume histograms on a display comprises displaying a dose volume histogram line on the display for each of the at least two structure dose volume histograms.

3. The method of claim 2 wherein detecting when the user directly manipulates the at least one of the at least two structure dose volume histograms comprises detecting when the user drags a structure dose volume histogram line on the display.

4. The method of claim 1 wherein using the virtual set of optimization objectives comprises, at least in part, creating the virtual set of optimization objectives in response to detecting when the user directly manipulates at least one of the at least two structure dose volume histograms on the display.

5. The method of claim 1 wherein using the virtual set of optimization objectives to optimize the radiation therapy treatment plan includes, at least in part, using the virtual set of optimization objectives to favor holding at least one of the structure dose volume histograms in a same position.

6. The method of claim 5 wherein using the virtual set of optimization objectives comprises, at least in part, using a location to where the user manipulated the at least one of the at least two structure dose volume histograms to define a new dose volume histogram objective.

7. The method of claim 1 wherein administering the radiation therapy to the patient will entail moving a radiation source with respect to the patient along a particular trajectory to a plurality of different exposure fields, the method further comprising using the control circuit to:
   use only a low-resolution approximate geometry to represent the particular trajectory when initially optimizing the radiation therapy treatment plan;
   subsequently use a high-resolution geometry to represent the particular trajectory to further optimize the radiation therapy treatment plan.

8. The method of claim 7 wherein the particular trajectory comprises an arc-shaped trajectory.

9. The method of claim 7 wherein:
   the low-resolution approximate geometry is formed by dividing the particular trajectory into only a low number of subparts;
   the high-resolution geometry is formed by dividing the particular trajectory into a greater number of subparts.

10. The method of claim 9 wherein using only the low-resolution approximate geometry to represent the particular trajectory when initially optimizing the radiation therapy treatment plan yields as an output, at least in part, a set of fluence maps corresponding to particular locations of the particular trajectory.

11. The method of claim 10 wherein the particular locations of the particular trajectory comprise, at least in the majority, key angles.

12. The method of claim 10 wherein the output further comprises dose distribution information and dose volume histograms per structure.

13. The method of claim 1 further comprising using the control circuit to use weighted optimization objectives to optimize the radiation therapy treatment plan.

14. The method of claim 13 further comprising using historical information to produce the weighted optimization objectives.

15. The method of claim 14 wherein the historical information provides an estimation regarding structure dose volume histograms that are achievable for the patient.

16. The method of claim 15 wherein using the weighted optimization objectives to optimize the radiation therapy treatment plan includes, at least in part, influencing which parts of at least one of the at least two structure dose volume histograms are permitted to change to a greater extent than other parts of the at least one of the at least two structured dose volume histograms during user interaction.

17. The method of claim 16 wherein the at least one of the at least two structure dose volume histograms is represented as a line and the weighted optimization objectives are distributed along the line.

* * * * *